United States Patent [19]

Wilson

[11] Patent Number: 5,198,354
[45] Date of Patent: Mar. 30, 1993

[54] CLONING THE BAN I RESTRICTION AND MODIFICATION GENES

[75] Inventor: Geoffrey G. Wilson, Boxford, Mass.

[73] Assignee: New England Biolabs, Inc., Beverly, Mass.

[21] Appl. No.: 699,145

[22] Filed: May 13, 1991

Related U.S. Application Data

[60] Continuation of Ser. No. 323,114, Mar. 13, 1989, Pat. No. 5,180,673, which is a continuation of Ser. No. 826,892, Feb. 6, 1986, abandoned, which is a division of Ser. No. 707,079, Mar. 1, 1985, abandoned.

[51] Int. Cl.$^5$ .................... C12N 9/22; C12N 15/55
[52] U.S. Cl. .................... 435/199; 435/252.33; 435/320.1; 435/193; 536/23.2; 536/23.7
[58] Field of Search ............... 435/122.3, 199, 252.3, 435/252.33, 320.1, 193; 935/29, 73, 80; 536/27

[56] References Cited

PUBLICATIONS

Sygisaki, H. et al., (1982), Nucl. Acids Res., 10(19), 5747–5752.
Walder, A. Y., et al., (1983), J. Biol. Chem., 258(2), 1235–1241.
Mann, M. B. et al., (1978), Gene, 3, 78–112.
Kessler, C., et al., (1985), Gene, 33, 1, 32.

Primary Examiner—Charles L. Patterson, Jr.
Attorney, Agent, or Firm—Gregory D. Williams; David G. Conlin

[57] ABSTRACT

Methods for cloning restriction enzymes and their corresponding modification enzymes by selecting clones resistant to in vitro digestion by the restriction enzyme and subsequent screening to identify those clones containing the restriction gene.

8 Claims, 7 Drawing Sheets

ORGANIZATION pHae II 4-11 R⁺ M⁺ FRAGMENTS

Hind III DOUBLE DIGESTS OF pHae II 4-11

NO SITES FOR

| | |
|---|---|
| Eco RI | Bam HI |
| Hae III | Sph I |
| Pvu II | Ban II |
| Bst EII | Hpa I |
| Cla I | Sac I |
| Sac II | Xba I |
| Xho I | |

| | UNITS OF Hae II per ml EXTRACT | | | |
|---|---|---|---|---|
| | METHYLASE | | ENDONUCLEASE | |
| | 30° | 43° | 30° | 43° |
| | 600 | <300 | 300 | <30 |
| | 600 | 3000 | 300 | 100,000 |
| | 600 | 3000 | 300 | 100,000 |

CLONING THE BAN I RESTRICTION AND MODIFICATION GENES

This is a continuation of copending application Ser. No. 07/323,114 filed in Mar. 13, 1989, now U.S. Pat. No. 5,180,673 which is a continuation of Ser. No. 06/826,892, filed Feb. 6, 1986, now abandoned, which is a divisional of Ser. No. 06/707,079, filed Mar. 1, 1985, now abandoned, the disclosure of which is incorporated herein by reference.

BACKGROUND OF THE INVENTION

This invention relates to clones which produce restriction enzymes and/or modification enzymes, to methods of producing such clones and to methods of producing the restriction and/or modification enzymes from the clones. This invention also relates, more specifically, to clones for the Hae II restriction endonuclease and modification methylase and for the Taq I restriction endonuclease and modification methylase, and related methods for the production of these clones and enzymes.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Close to one hundred different restriction endonucleases have been identified among the many hundreds of bacterial species that have been examined to date.

Bacteria tend to possess at most only a small number of restriction endonucleases per species. The endonucleases typically are named according to the bacteria from which they are derived. Thus, the species *Haemophilus aegyptius*, for example, synthesizes 3 different restriction endonucleases, named Hae I, Hae II and Hae III. Those enzymes recognize and cleave the sequences (AT)GGCC(AT), PuGCGCPy and GGCC respectively. *Escherichia coli* RY13, on the other hand, synthesizes only one enzyme, EcoR I, which recognizes the sequence GAATTC.

In nature, restriction endonucleases play a protective role in the welfare of the bacterial cell. They enable bacteria to resist infection by foreign DNA molecules like viruses and plasmids that would otherwise destroy or parasitize them. They achieve this resistance by scanning the lengths of the infecting DNA molecule and cleaving them each time that the recognition sequence occurs. The break-up that takes place disables many of the infecting genes and renders the DNA susceptible to further degradation by non-specific exonucleases.

A second component of bacterial protective systems are the modification methylases. These enzymes are complimentary to restriction endonucleases and they provide the means by which bacteria are able to identify their own DNA and distinguish it from foreign, infecting DNA. Modification methylases recognize and bind to the same nucleotide recognition sequences as the corresponding restriction endonucleases, but instead of breaking the DNA, they chemically modify one or other of the nucleotides within the sequence by the addition of a methyl group. Following this methylation, the recognition sequence is no longer bound or cleaved by the restriction endonuclease. The DNA of a bacterial cell is always fully modified, by virtue of its modification methylases, and it is therefore completely insensitive to the presence of the endogenous restriction endonucleases. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating restriction endonuclease clones is to develop a simple and reliable method to identify such clones within complex 'libraries', i.e. populations of clones derived by 'shotgun' procedures, when they occur at frequencies as low as $10^{-4}$ to $10^{-3}$. Preferably, the method should be selective, such that the unwanted majority of clones are destroyed while the rare desirable clones survive.

Some investigators have used bacteriophage infection as a means of selectively isolating restriction endonuclease clones (Walder et al., Proc. Nat. Acad. Sci. 74 1503–1507 (1981), Mann et al., Gene 3: 97–112 (1981). Since the presence of restriction-modification systems in bacteria enable them to resist infection by bacteriophages, cells that carry cloned restriction-modification genes can in principle be selectively isolated as survivors from libraries that have been exposed to phage. This method has been found, however, to have only limited value. Specifically, it has been found that cloned restriction-modification genes do not always manifest sufficient phage resistance to confer selective survival.

Because purified restriction endonucleases, and to a lesser extent, modification methylases, are useful tools for characterizing and re-arranging DNA in the laboratory, there is a commercial incentive to develop strains of bacteria that synthesize these enzymes in abundance. Such strains would be useful because they would simplify the task of purification as well as providing the means for production in commercially useful amounts.

SUMMARY OF THE INVENTION

In accordance with the present invention, there is provided a novel approach to the production of restriction enzymes and/or their corresponding modification enzymes by cloning genes that encode them and arranging for the genes to be expressed at elevated levels. More specifically, there is provided methods of cloning these enzymes, the clones so produced and methods of producing the enzymes themselves which comprises forming a library containing the DNA coding for the desired restriction enzyme, isolating those clones which contain the corresponding modification gene, and screening clones containing the modification gene for the presence of the restriction gene.

The application of this method to the Hae II and Taq I restriction and modification genes of *Haemophilus aegyptius* and *Thermus aquaticus* respectively is described in detail, together with the resulting strains that form the basis of a new and useful process for purifying the Hae II and Taq I restriction and modification enzymes.

DETAILED DESCRIPTION OF THE INVENTION

Figure 1:
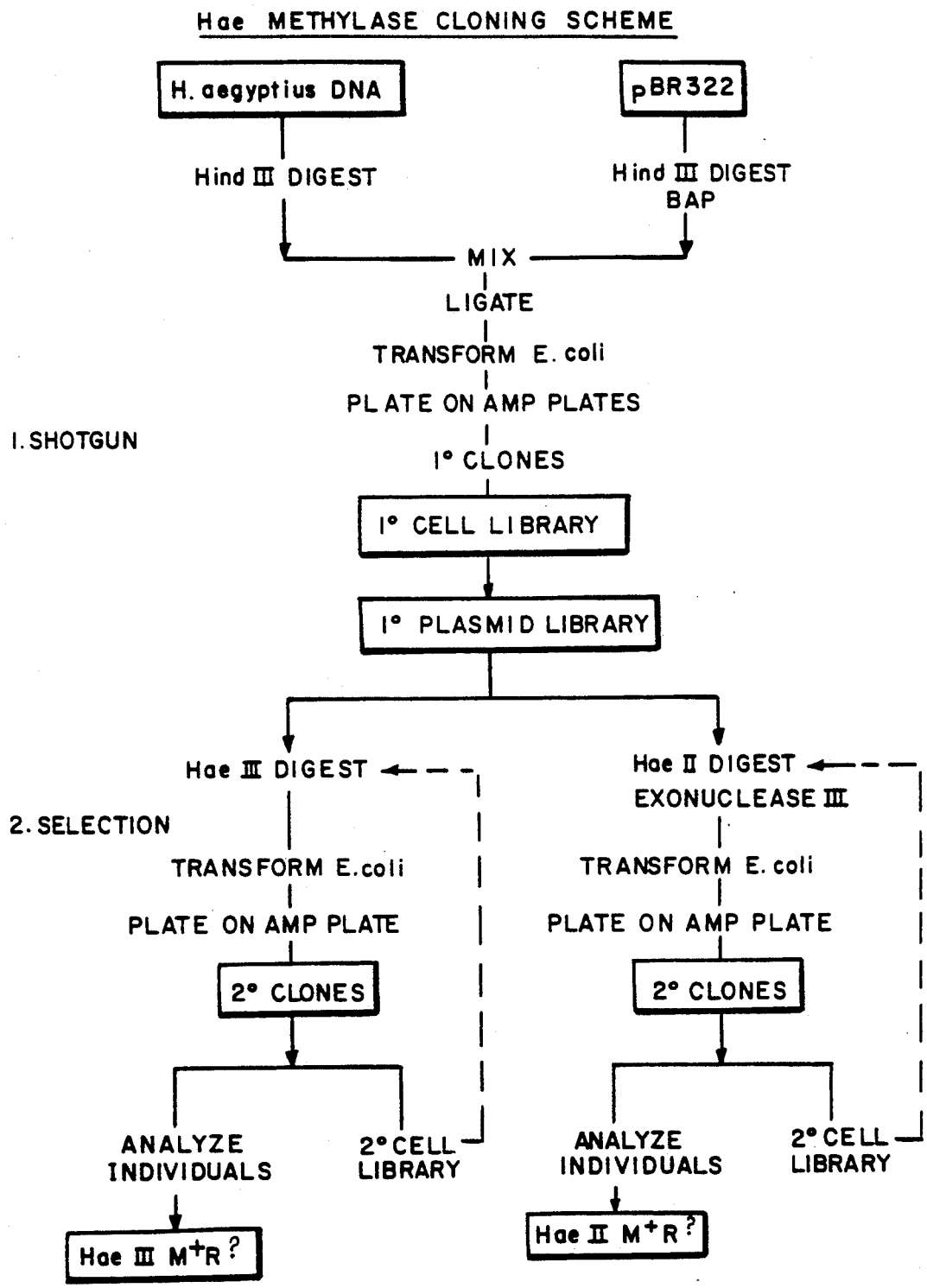
FIG. 1 illustrates the scheme for cloning Hae II restriction/modification genes.

The present invention provides a novel approach for cloning restriction and/or modification genes and harvesting enzymes from clones produced thereby. This approach takes advantage of the fact that clones which contain modification genes will methylate their own DNA within the corresponding restriction gene's recognition sequence if such sequences are present in the clone. Such clones will therefore be resistant to digestion in vitro by the corresponding restriction endonuclease. It therefore follows that restriction endonuclease digestion of these clones will result in the selective survival of methylase-encoding clones. Moreover, if the methylase-encoding clone also contains the corresponding restriction gene then such clones will also provide the means for expressing and harvesting the restriction enzyme itself.

While not wishing to be bound by theory, it is believed that restriction endonuclease genes occur in close proximity to their corresponding modification methylase gene in the bacterial chromosome, and that the two genes are therefore likely to remain linked together during cloning experiments. Thus, it is believed that clones that acquire methylase genes are quite likely to simultaneously acquire the corresponding endonuclease gene provided that the fragment of DNA they receive during cloning is reasonably large.

In accordance with the present invention, it has been found that restriction genes and their corresponding modification genes are physically close in the DNA of many bacteria. This being the case, in practicing the present invention, selection for methylase-containing cells can be used as a simple and reliable method for selectively co-isolating methylase and endonuclease clones. In brief, selection of methylase-carrying clones from libraries which also contain DNA fragments coding for the corresponding restriction genes frequently results in the isolation of clones that carry both the methylase and the restriction endonuclease genes corresponding to the same DNA sequence. Methylase-selection is therefore an indirect way of selecting restriction endonuclease clones.

The methods described herein by which restriction genes are preferably cloned and expressed include the following steps:

1. The DNA of the bacterial species to be cloned is purified.

2. The DNA is digested partially with a convenient restriction endonuclease.

3. The resulting fragments are ligated into a cloning vector, such as pBR322, and the mixture is used to transform an appropriate host cell such as *E. coli* cells.

4. The DNA/cell mixture is plated on antibiotic media selective for transformed cells. After incubation, the transformed cell colonies are scraped together into a single culture, the primary cell library.

5. The recombinant plasmids are purified in toto from the primary cell library to make a primary plasmid library.

6. The plasmid library is then digested to completion in vitro with the restriction enzyme whose corresponding methylase gene is sought. Exonuclease and/or phosphatase may also be added to the digestion to enhance the destruction of non-methylase clones.

7. The digested DNA is transformed into *E. coli* and transformed colonies are again obtained by plating on antibiotic plates. Some of these colonies—secondary cell individuals—may be picked and their DNA analyzed for the presence of the modification and/or restriction genes. The remaining colonies may be scraped together to form a secondary cell library from which a secondary plasmid library may be subsequently prepared.

8. The secondary plasmid library may be redigested with restriction endonuclease (with or without exonuclease or phosphatase) to repeat the selection, leading to the recovery of tertiary cell individuals, tertiary cell libraries and tertiary plasmid libraries.

9. Each round of restriction endonuclease digestion causes selective destruction of non-methylase clones, and results in an increase in the relative frequency of the desired methylase-carrying clones.

10. Surviving colonies among the secondary and tertiary population are picked and analyzed for the presence of the methylase gene. If it is found to be present, they are further analyzed for the simultaneous presence of the restriction gene that is presumed to be linked to the methylase gene.

11. Methylase screening may be performed by four simple tests:

(a) The recombinant plasmid DNA molecule of the clone may be purified and exposed in vitro to the selecting restriction endonuclease to establish that it is resistant to digestion. Provided that the plasmid vector carries several sites for that endonuclease, resistance indicates modification, rather than mutational site loss.

(b) The recombinant plasmid may be digested with the enzyme initially used to fragment the donor bacterial DNA. The fragments present in the clone should be comprehensible, sufficiently large to encode a methylase gene (i.e., over 1 Kilobase pair) and, most important, common to a variety of independently-formed clones: the same fragment or fragments should be present among all the clones.

(c) The total chromosomal DNA of the clone may be purified and exposed to the selective restriction endonuclease. If the clone carries the methylase gene, the bacterial chromosome should be fully methylated and, like the plasmid, should be found to be resistant to digestion.

(d) The cell extract from the clone may be prepared and assayed in vitro for methylase activity. (Methylase protection and radioactive labelling.) Methylase activity should be found.

12. Restriction endonuclease screening may be carried out in two ways:

(a) The cell extract from the clone may be prepared and assayed in vitro for its ability to digest sensitive DNA. Restriction endonuclease activity should be found.

(b) The cells themselves may be tested in vivo for their ability to resist phage infection. Resistance to phage infection indicates the presence of a restriction-modification system.

Although the above-outlined steps represent the preferred mode for practicing the present invention, it will be apparent to those skilled in the art that the above-described approach can vary in accordance with techniques known in the art.

Clones containing the restriction and modification genes of Ban I, Hha II, Hind III, Hinf I and Msp I and have also been produced in accordance with the present invention. The source of DNA containing the above genes was *Bacillus aneurinolyticus* (Ban I) (Institute of Applied Microbiology, IAM 1077, Sugisaki, H., Maekawa, Y., Kanazawa. S. and Takanami. M. (1982) Nucleic Acids Res. 10, 5747-5752), *Haemophilus haemolyliticus* (Hha II) (ATCC 10014), *Haemophilus influenzae* Rd (Hind III) (ATCC 33928), *Haemophilus influenzae* Rf (Hinf I) (ATCC 17947) and *Moraxella species* (Msp I) (ATCC 53043). A sample of the clone containing the restriction and modification gene Gan I has been deposited at the ATCC under ATCC Accession No. 75276 which was deposited on Jul. 17, 1992.

It should be noted that occasionally, the general approach above may, on occasion, yield no methylase clones at all. However, it has been generally found that it does yield methylase clones and among these, about half tend to also carry the corresponding restriction gene. At present, it is not clear whether the occasional failures result from technical difficulties or from fundamental biological problems such as non-linkage, failure to express, etc.

One important factor, however, that has been found to affect the successful cloning of restriction and modification genes is the strain of *E.coli* that is used as the host. Many bacteria have restriction-modification systems, including *E. coli*. The most common system in *E.coli* is the host specific determinant or "Hsd" system, but other systems, notably P1, and the EcoR-series, also occur (Roberts, R. J., Nucl. Acids Res. 12S:R167-204 (1984). These systems interfere with cloning because they cause the destruction of the incoming DNA during transformation, resulting in low numbers of transformants and unrepresentative libraries. In general, therefore, in practicing the present invention, the preferred *E.coli* is one in which the restriction systems have been inactivated through mutation or loss. Preferred strains in which these systems have been inactivated or are absent, and which may be used for general cloning purposes, include HB101(hsdR−M−) ATCC 33694, RR1(hsdR−M−) ATCC 31343, K802(hsdR−M+) ATCC 33526, K803(hsdR−M−) ATCC 27065 and MM294(HsdR−M+) ATCC 33625.

With particular regard to the cloning of foreign restriction and/or modification genes into *E.coli*, in accordance with another embodiment of the present invention it has been found that there is an additional system which interferes with successful cloning. The system is obscure and is referred to as the "Rgl" system (Revel, H. R., *Bacteriophage T*4, pp. 156-165 American Society of Microbiology (1983) and Revel et al., Annual Review of Genetics 4:177-192 (1970)). More specifically, the *E.coli* Rgl system restricts DNA molecules that bear methylated cytosine residues, and thus destroys the very self-methylated plasmid clones to be isolated. In order to clone such methylase genes, therefore, it is preferred to use *E.coli* hosts that are defective for both the Hsd (general) system and the Rgl (specific) system. Not all cloned methylase genes are susceptible, however. Specifically, those which methylate adenine residues appear to be entirely unaffected by the Rgl system in contrast to those which methylate cytosine residues.

While not wishing to be bound by theory, it is believed that the Rgl system is made up of two components, designated "Rgl A" and "Rgl B". It appears that Rgl B restricts many cytosine-methylase clones while Rgl A is presently known to restrict only one clone (Hpa II).

In choosing a host for cloning the restriction and/or modification genes of an uncharacterized restriction-modification system, or one that is known to methylate at cytosines, a preferred host is an *E.coli* strain that is triply-mutant, i.e., one that lacks the Hsd, Rgl A and Rgl B systems. Such strains include K802. If, on the other hand, the modification system is known to be an adenine-methylase type system, the Rgl activity of the hose can be ignored. The choice of host thus depends upon the character of the modification gene to be cloned. It will be appreciated by those skilled in the art that such hosts are not only useful in the above described approach to cloning restriction and/or modification genes but will be useful in other known procedures.

Thus, in accordance with another embodiment of the present invention, there is provided a method of cloning cytosine-type modification genes and/or their corresponding restriction endonuclease genes comprising constructing the clone and propagating it in an Rgl-deficient strain of *E.coli*. Table I summarizes the suitability of several strains of *E.coli* for the cloning of several modification genes.

TABLE I

| Type of Modification Methylase | Restriction-Modification System | Suitable Strains of *E. coli* | | |
|---|---|---|---|---|
| | | K802 (hsdR−, rglA−B−) | RR1 (hsdR−, rglA+B−) | MM294 (hsdR−, rglA+B+) |
| Adenine-Methylase (known or presumed) | EcoR I | suitable | suitable | suitable |
| | Hha II | | | |
| | Hind III | | | |
| | Hinf I | | | |
| | Pst I | | | |
| | Sal I | | | |
| | Taq I | | | |
| Cytosine-Methylase (known or presumed) | Alu I | suitable | suitable | unsuitable |
| | Ban I | | | |

TABLE I-continued

| Type of Modification Methylase | Restriction-Modification System | Suitable Strains of E. coli | | |
|---|---|---|---|---|
| | | K802 (hsdR$^-$, rglA$^-$B$^-$) | RR1 (hsdR$^-$, rglA$^+$B$^-$) | MM294 (hsdR$^-$, rglA$^+$B$^+$) |
| (Rgl B-sensitive) | Ban II | | | |
| | Bgl I | | | |
| | Dde I | | | |
| | FnuD II | | | |
| | Hae II | | | |
| | Hae III | | | |
| | HgiA I | | | |
| | Hha I | | | |
| | Msp I | | | |
| | Nla IV | | | |
| Cytosine-Methylase (Rgl A-sensitive) | Hpa II | suitable | unsuitable | unsuitable |

The following examples are given to additionally illustrate embodiments of the present invention as it is presently preferred to practice. It will be understood that these examples are illustrative, and that the invention is not to be considered as restricted thereto except as indicated in the appended claims.

EXAMPLE I

Cloning of the Hae II Restriction-Modification Genes

FIG. 1 illustrates the Hae II Methylase cloning scheme in accordance with the above-described method for cloning restriction genes. The Hae II clones were prepared as follows:

1. DNA purifications: To prepare the DNA of *Haemophilus aegyptius* (ATCC 11116), 5 gm of freshly-grown cell paste was resuspended in 20 ml of 25% sucrose, 50 mM Tris, pH 8.0. 10 ml of 0.25M EDTA, pH 8.0 plus 6.0 ml of 10 mg/ml lysozyme in 0.25M Tris pH 8.0, was added. The suspension was left on ice for two hours. Thereafter, 24 ml of lysis mix (1% Triton X-100, 50 mM Tris, pH 8.0, 67 mM EDTA) plus 5 ml of 10% SDS was added and mixed to allow the cells to lyse. 70 ml of freshly-equilibrated phenol was then added and the solution was emulsified by shaking. 70 ml of chloroform was added and the solution was again emulsified by shaking. The mixture was then centrifuged at 10K rpm for 30 minutes and the viscous upper layer containing DNA was transferred to a fresh bottle and re-extracted with phenol/chloroform twice more. The upper DNA layer was transferred to dialysis tubing and dialyzed against four changes of 1X DNA buffer (10mM Tris, 1mM EDTA, pH 8.0) over 24 hours.

The dialysed DNA solution was transferred to a beaker and 1/100th volume of 10 mg/ml RNase was added to achieve a final concentration of 100 μg/ml. The solution was incubated at 37° for 1 hour to digest the RNA. 5M NaCl was then added to achieve 0.4M final concentration and 0.55 volumes of isopropanol was then layered on top of the solution. The DNA was spooled out of this mixture with a glass rod, then dissolved in 15 ml of 1X DNA buffer and stored at 4° C.

2. Partial digestion: The purifed DNA was titrated with Hind III to achieve partial digestion as follows: 2.0 ml of DNA at 100 μg/ml in 10 mM Tris pH 7.5, 10 mM MgCl$_2$, 50 mM NaCl, 10 mM mercaptoethanol buffer was dispensed into ten, 200 μl aliquots. To the first tube was added 40 units of Hind III to achieve 2 units per μg of DNA. To the second tube was added 20 units of Hind III (1 unit/ug), and so on, each succeeding tube receiving half of the previous amount of Hind III. The tubes were incubated at 37° C. for one hour, then heat-treated at 72° C. for 15 minutes and 10 μl from each analyzed by agarose gel electrophoresis. Tubes exhibiting moderate, but incomplete, digestion were chosen as the source of partial digest fragments for cloning. (These were the 0.13 unit/ug and 0.06 unit/ug tubes. The two solutions were mixed together and used as described below.)

3. Ligation: The fragmented DNA was ligated to pBR322 as follows: 4.0 μg of Hind III partially digested *H.aegyptius* DNA (40 μl) was mixed with 2.0 μg of Hind III-cleaved and dephosphorylated pBR322 (10 ul). 10 μl of 10% ligation mix (500 mM Tris, pH 7.5, 100 mM MgCl$_2$, 100 mM DTT, 5 mM ATP) was added plus 40 μl of sterile distilled water to bring the final volume to 100 μl. 5 μl of T4 DNA ligase was added and the mixture allowed to incubate at 16° C. for 4 hours. Ten, 10 μl quantities were used to transform *E. coli* strain RR1 as follows: Each 10 μl aliquot was mixed with 100 μl of SSC/CaCl$_2$ (50 mM NaCl, 5 mM Na$_3$Citrate, 67 mM CaCl$_2$) on ice and 200 μl of ice-cold competent *E. coli* RR1 cells was added. After a 2-minute heat shock at 43° C., the cells were diluted into 5 ml of Luria-broth (L-broth) and grown to saturation at 37° C.

4. Primary Cell Library: The transformed cell cultures were centrifuged, resuspended in 250 μl volumes and plated onto Luria-agar (L-agar) plates containing 100 μg/ml ampicillin. After overnight incubation at 37° C., the plates were each flooded with 2.5 ml of 10 mM Tris, pH 7.5, 10 mM MgCl$_2$ and the transformed colonies were scraped together and pooled to form the primary cell library.

5. Primary Plasmid Library: The primary plasmid library was prepared as follows: 2.5 ml of the primary cell library was innocculated into 500 ml of L-broth containing 100 μg/ml ampicillin. The culture was shaken overnight at 37° C. then centrifuged at 4K rpm for 5 minutes. The supernatant was discarded and the cell pellet was resuspended in 10 ml of 25% sucrose, 50 mM Tris, pH 8.0, at room temperature. 5 ml of 0.25M EDTA, pH 8.0, was added, followed by 3 ml of 10 mg/ml lysozyme in 0.25M Tris, pH 8.0. The solution was left on ice for 1 hour, then 12 ml of lytic mix (1% Triton X-100, 50 mM Tris, pH 8.0, 67 mM EDTA) was forcefully pipetted in and the cell suspension gently swirled to achieve lysis. After lysis, the mixture was transferred to a 50 ml plastic centrifuge tube and spun at 17K rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two ⅝ in.×3 in. polyallomer centrifuge tubes and sealed. These were then spun in the Ti70 rotor for 42 hours at 50K rpm, 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of ice-cold N-Butanol.

The extracted solution was transferred to dialysis tubing and dialyzed for 24 hours against 4 changes of 1X DNA buffer. The dialyzed DNA solution was then transferred to a pre-weighed 50 ml sterile centrifuge tube and its volume measured. 5M NaCl was added to a final concentration of 0.4M, then 2 volumes of isopropanol was added and mixed. The solution was stored overnight at −20° C. to precipitate the DNA. After precipitation, the solution was spun at 15K rpm, 0° C. for 15 minutes and the supernatant discarded. The tube was left on the bench to air-dry for 15 minutes, then 750 $\mu$l of sterile distilled water was added. After the pellet had dissolved, 8 $\mu$l of 100X DNA buffer was added and the solution was transferred to an Eppendorf tube and stored at −20° C. The DNA concentrations of plasmids prepared in this way were found to be approximately 100 to 200 ug/ml.

6. Digestion of Plasmid Pool: The primary plasmid pool was digested to destroy non-Hae II methylase clones as follows: The plasmid DNA was diluted to 50 $\mu$g/ml in 10 mM Tris pH 7.5, 10 mM MgCl$_2$, 10mM mercaptoethanol, 50 mM NaCl. A total of 500 $\mu$l was prepared and dispensed into 5 tubes, 100 $\mu$l each. 75 units of Hae II was added to the first tube to achieve 15 units/$\mu$g DNA. 38 units of Hae II were added to the second tube and so on, each tube receiving half of the previous amount. The tubes were incubated at 37° C. for 1 hour.

7. Transformation: A 10 $\mu$l sample from each tube was used to transform *E. coli* RR1 in the manner described previously. The cell/DNA mixtures were plated onto L-agar plates containing 100 $\mu$g/ml ampicillin immediately after the heat step, without intermediate dilution and growth. After overnight incubation at 37° C., the plates were examined. Digestion of the plasmid library with Hae II was found to have reduced the number of transformants (i.e. the number of intact plasmids) by a factor of about $10^{-2}$. In later experiments, it was found that the addition of 2.5 units of exonuclease III (New England Biolabs, Inc., also available from BRL and IBI) or lambda exonuclease to each of the digestion tubes described above (section 6) enhanced the destruction of non-methylase clones and reduced the number of transformants by a factor of about $10^3$ to $10^4$. Approximately 30 individual colonies were picked from among the surviving colonies on the plates that had suffered the greatest attrition (15 units Hae II/$\mu$g and 7.5 units Hae II/$\mu$g, plus or minus exonuclease). Each colony was inoculated into 10 ml of L-broth containing ampicillin to prepare a miniculture and was streaked onto L-agar plate containing ampicillin to prepare a master stock.

8. Secondary Populations: The remaining colonies were scraped together to form a secondary cell library. This was used to prepare a secondary plasmid library in the same manner as described for the preparation of the primary plasmid library.

9. Analysis of Secondary Plasmid Libraries: The secondary Hae II libraries were not used further in this particular experiment. As a general rule, however, it is helpful to analyze secondary plasmid libraries by digestion and gel electrophoresis. Such analysis can be useful for determining whether a significant proportion of the population carries a common fragment and exhibits resistance to restriction endonuclease digestion.

10. Analysis of secondary individuals: Approximately 30 of the surviving colonies among the secondary cell individuals were grown up into 10 ml cultures (section 7) and the plasmids that they carried were prepared by the following miniprep purification procedure, adapted from the method of Birnboin and Doly (*Nucleic Acids Res.* 7: 1513 (1979)).

Miniprep Procedure: Each culture was processed as follows: The 10 ml overnight culture was pelleted at 8K rpm for 5 minutes. The supernatant was poured off and the cell pellet was resuspended in 1.0 ml of 25 mM Tris, 10 mM EDTA, 50mM glucose, pH 8.0, containing 1 mg/ml lysozyme. After 10 minutes at room temperature, 2.0 ml of 0.2M NaOH, 1% SDS was added and the tube was shaken to lyse the cells, then placed on ice. Once the solution had cleared, 1.5 ml of 3M sodium acetate, pH 4.8, was added and shaken. The precipitate that formed was spun down at 15K rpm, 4° C. for 10 minutes. The supernatant was poured into a centrifuge tube containing 3 ml of isopropanol and mixed. After 10 minutes at room temperature, the tube was spun at 15K rpm for 10 minutes to pellet the precipitated nucleic acids. The supernatant was discarded and the pellet was air-dried at room temperature for 30 minutes. Once dry, the pellet was resuspended in 850 $\mu$l of 10 mM Tris, 1 mM EDTA, pH 8.0. 75 $\mu$l of 5M NaCl was added and the solution was transferred to an Eppendorf tube containing 575 $\mu$l of isopropanol and again precipitated for 10 minutes at room temperature. The tube was then spun for 45 seconds in a microfuge, the supernatant was discarded and the pellet was air-dried. The pellet was then dissolved in 50 $\mu$l of 10 mM Tris, 1 mM EDTA, pH 8.0, containing 100 $\mu$g/ml RNase and incubated for 1 hour at 37° C. to digest the RNA. The DNA was precipitated once more by the addition of 50 $\mu$l of 5M NaCl followed by 350 $\mu$l of isopropanol. After 10 minutes at room temperature, the DNA was spun down by centrifugation for 45 seconds, the supernatant was discarded and the pellet was redissolved in a final solution of 150 $\mu$l of 10 mM Tris 1 mM EDTA, pH 8.0. The plasmid minipreps were subsequently analyzed by digestion with Hind III and Hae II.

11. Methylase Gene Clones: Many of the plasmids that were analyzed were found to carry random, Hind III fragments of Haemophilus DNA and to be sensitive to digestion by Hae II. These plasmids were spurious survivors of no further interest. (Their presence was found to be markedly reduced in later experiments in which exonuclease was used during the Hae II digestion-selection stage.) The remaining plasmids, however, were found to be both resistant to Hae II and to carry at least two Hind III fragments of approximately 3.1 Kb and 2.9 Kb in length. These plasmids were subsequently shown to carry both the Hae II modification methylase and restriction endonuclease genes.

Figure 2:
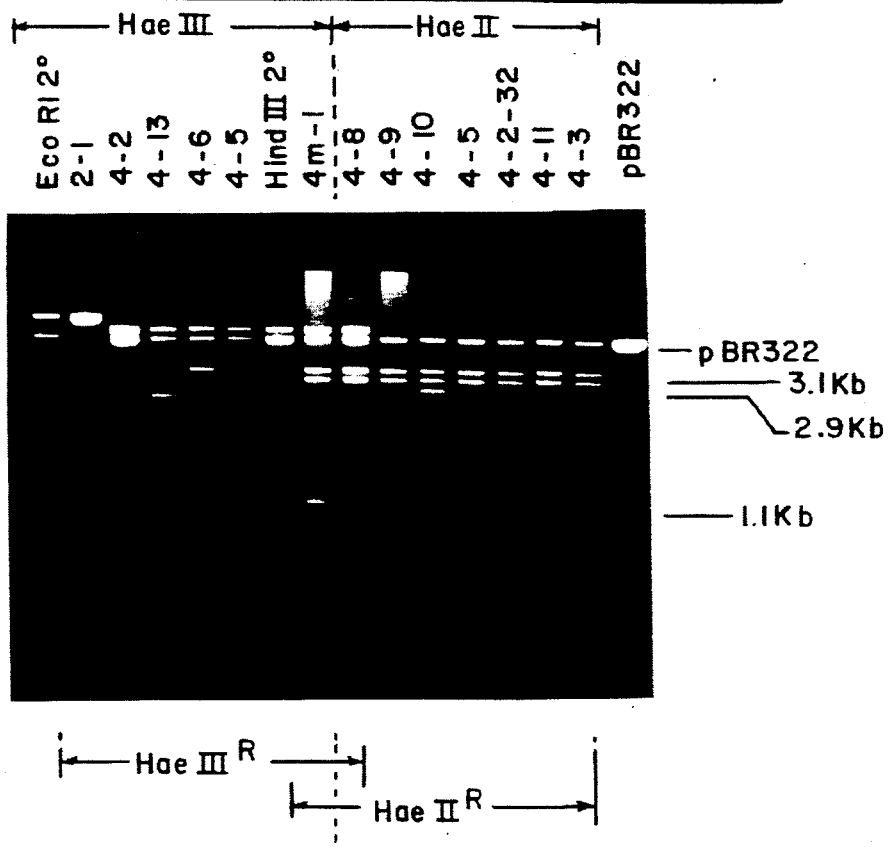
FIG. 2 shows reproduction of photographs of gels of Hind III digests of several Hae II restriction/modification and Hae II modification clones.
Figure 2:
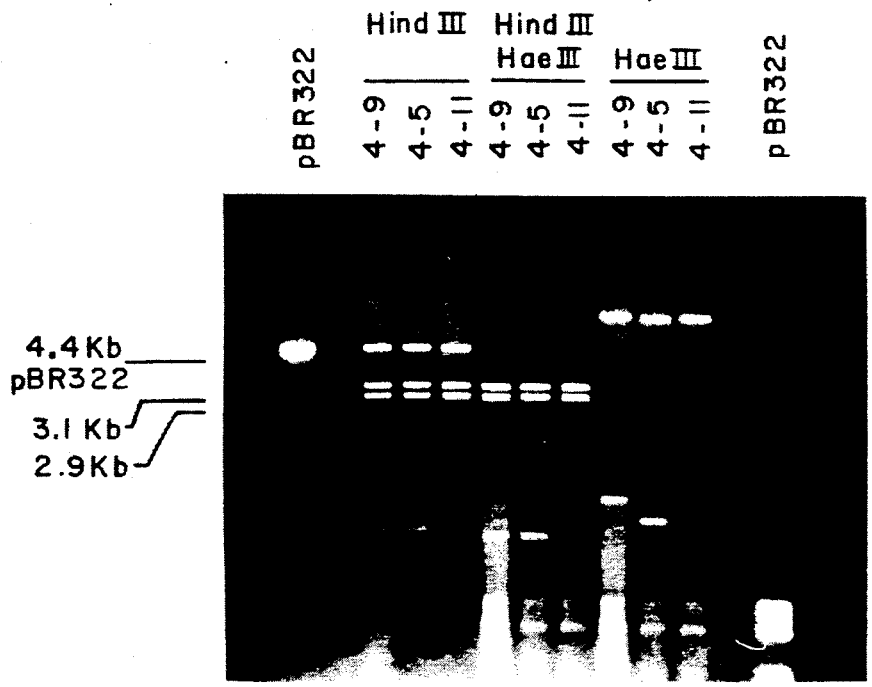
Figure 3:
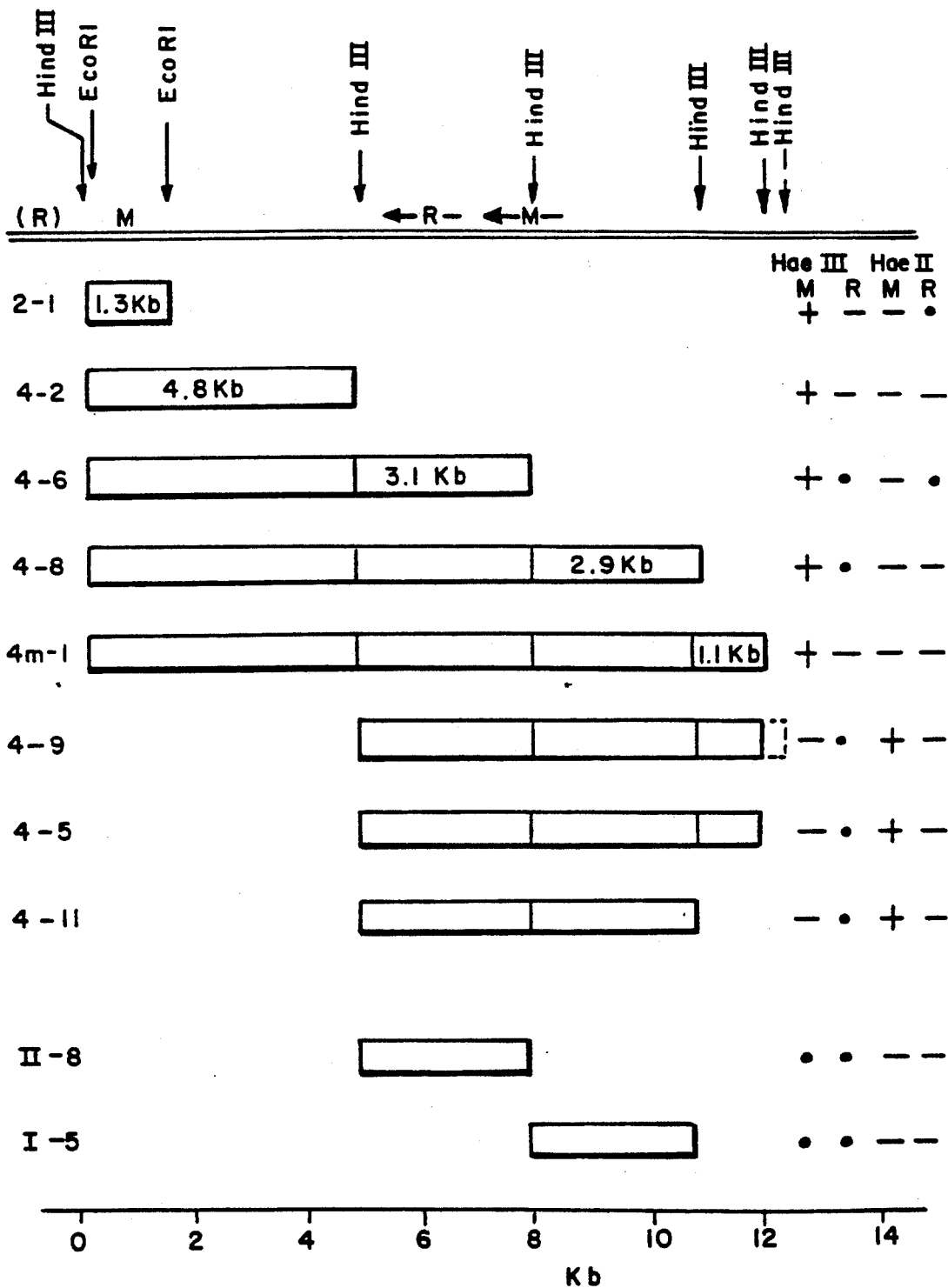
FIG. 3 illustrates the organization of Hae II and Hae III restriction and modification genes of clones produced in accordance with the present invention.

In a parallel series of experiments, clones carrying the Hae III methylase gene were also selected and isolated (FIG. 1). These clones were found to carry a Hind III fragment of approximately 4.8 Kb. Several clones were isolated that carried both the Hae III and the Hae II methylase genes, and these were found to carry both the 4.8 Kb fragment and the two 3.1 Kb and 2.9 Kb fragments. The isolation of these latter clones suggests that in *H. aegyptius* the Hae II restriction and modification genes are linked to at least the Hae III methylase gene. No clones were isolated which carried the Hae III restriction gene. FIG. 2 is a reproduction of a photograph of a gel of Hind III-digests of some of the Hae II restriction/modification and the Hae III modification clones. FIG. 3 summarizes the composition of some of the clones deduced from this, and similar analysis.

The clones that carried at least the 3.1 Kb and 2.9 Kb Hind III fragments (Hae II 4m-1, 4-8, 4-9, 4-10, 4-5, 4-11, 4-3 etc.) were judged to carry the Hae II methylase gene on the basis of (a) insensitivity to digestion by the Hae II restriction endonuclease and (b) in vitro assays of Hae II modification methylase activity. The methylase assays were performed as follows:

Methylase Assays: To assay for methylation three solutions were prepared:

10X Methylation buffer: 0.5M Tris, pH 7.5, 100 mM EDTA, 50 mM Mercaptoethanol.

Methylation reaction mix: Prepared fresh, for the analysis of 1 clone: 100 μl lambda DNA (500 μg/ml), 100 μl 10X methylation buffer, 1 μl 100 mM S-Adenosyl Methionine, 800 μl distilled water.

2X Hae II conversion buffer: 50 mM NaCl, 40 mM, $MgCl_2$, 15 mM Mercaptoethanol.

Cell extracts were prepared as follows: A 100 ml culture of the clone to be tested was grown overnight in L-broth plus 100 μg/ml ampicillin at 37° C. and the cells were pelleted by centrifugation at 4K rpm for 5 minutes. The supernatant was discarded and the pellet was resuspended in 5 ml of sonication buffer (10 mM Tris, pH 7.5, 10 mM Mercaptoethanol, 1 mM EDTA). Once resuspended, 0.5 ml of sonication buffer containing 10 mg/ml lysozyme was added. The suspension was swirled and left on ice for 1 hour.

A 1 ml sample was transferred to an Eppendorf tube and sonicated gently for two 10-second bursts to disrupt the cells. The tube was spun for 30 seconds in a microfuge and the supernatant was used as the cell extract.

To assay the extract, the methylation reaction mix was dispensed into 5 tubes, 150 ul into the first tube, and 102.5 ul into each of the remaining 4 tubes. 7.5 ul of the cell extract was added to the first tube, mixed, and 47.5 ul was removed and added to the next tube, mixed and so on. The first tube thus received 1 ul of extract per ug of DNA, the second tube, 0.3 ul/ug, the third tube, 0.1 ul/ug and so on. The tubes, each now containing 100 ul, were incubated at 37° C. for one hour, then heated to 72° C. for 10 minutes to stop the reactions. 100 ul of 2X conversion buffer, and 25 units of Hae II restriction enzyme, were then added to each tube. The solutions were again incubated at 37° C. for one hour, then a 20 ul sample of each was analyzed by gel electrophoresis. The clones were found to synthesize about 5000 units of Hae II methylase per gram of wet cell paste.

12. Restriction Gene Clones: The clones identified above (section 11) as carrying the Hae II modification methylase gene were also found to carry the Hae II restriction endonuclease gene. This was established by in vitro restriction endonuclease assays performed as follows:

Endonuclease Assays: To assay for endonuclease activity, two solutions were prepared:

10X Hae II Restriction endonuclease buffer: 100 mM Tris, pH 7.5, 100 mM $MgCl_2$, 100 mM Mercaptoethanol, 500 mM NaCl.

Digestion reaction mix: Prepared fresh, for the analysis of 1 clone: 100 ul lambda DNA (500 ug/ml), 100 ul 10X Hae II Restriction endonuclease buffer, 800 ul distilled water.

The cell extract was prepared in the manner described above for the methylation assay (section 11). To assay the extract, the digestion reaction mix was dispensed into 6 tubes, 150 ul into the first tube and 102.5 ul into each of the remaining 5 tubes. 7.5 ul of the extract was added to the first tube, mixed and 47.5 ul was removed and added to the next tube, mixed and so on. The first tube thus received 1 ul of extract per ug of DNA, the second tube, 0.3 ul/ug, the third tube, 0.1 ul/ug and so on. The tubes, each now containing 100 ul, were incubated at 37° for one hour, then a 20 ul sample of each was analyzed by gel elecrophoresis. The clones were found to synthesize about 3000 units of Hae II restriction endonuclease per gram of wet cell paste.

In tests with phages, the clones were found to resist phage infection to only a slight degree: The efficiency of plating of phage lambda was found to be between 0.1 and 0.5. (Clone 4m-1 (FIGS. 2 and 3) was exceptional. The efficiency of plating of phage lambda on 4m-1 was less than $10^{-4}$.).

EXAMPLE II

Overexpression of the Hae II Restriction and Modification Genes

Figure 4:
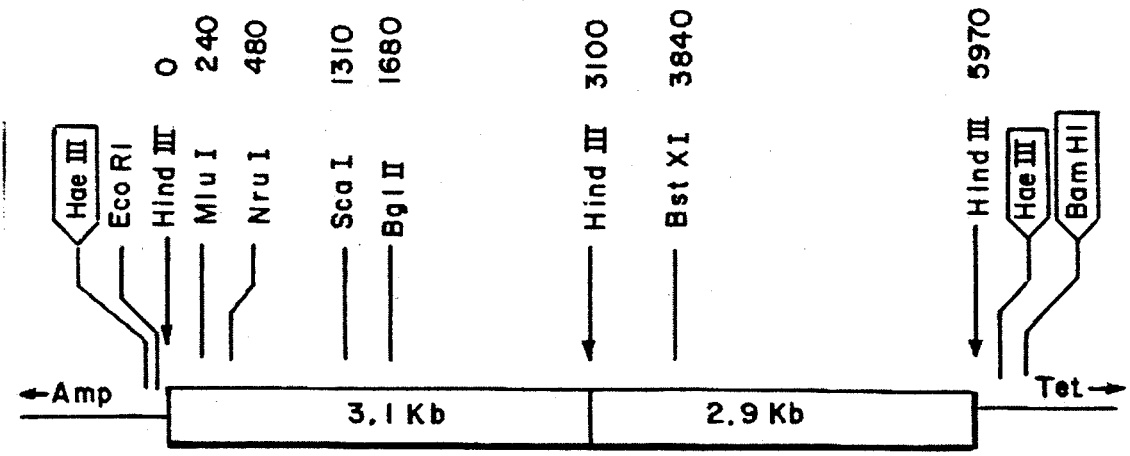
FIG. 4 illustrates the organization of the plasmid pHae II restriction/modification gene fragments as well as a reproduction of a photograph of a gel for Hind III double digests of pHae II.
Figure 4:
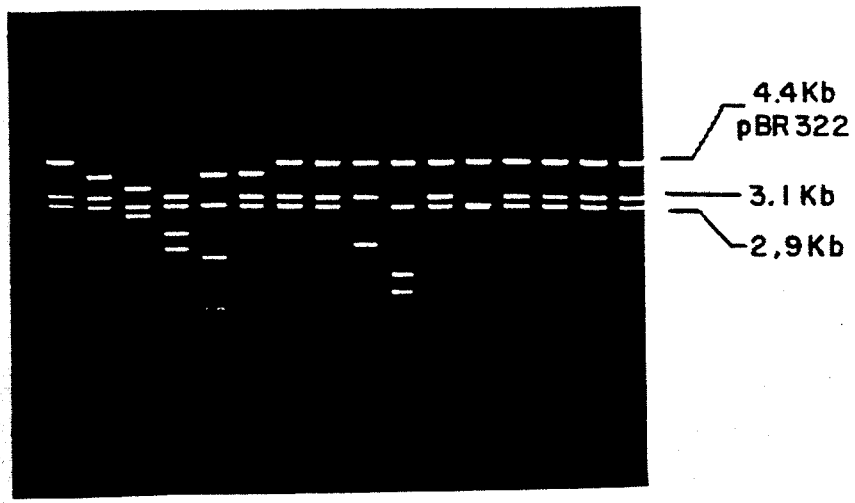

1. One of the clones obtained in Example I, designated pHae II 4-11 (FIGS. 3 and 4), was used for further analysis and for overexpression because it possessed the simplest structure. FIG 4 shows simplified restriction map of the two inserted Hind III fragments in this clone. The map was established by conventional double digest procedures.

Figure 5:
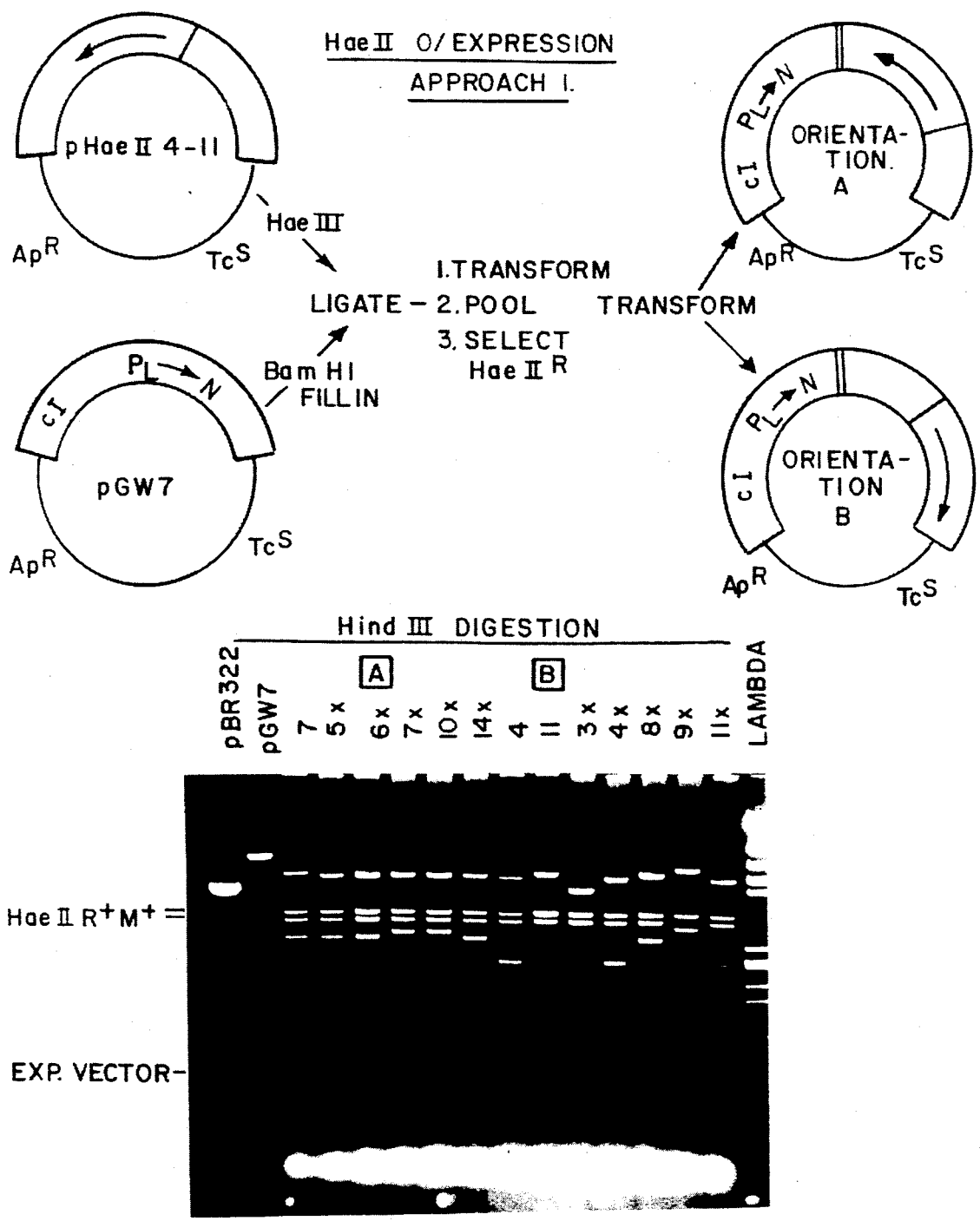
FIG. 5 illustrates a first approach to the overexpression of Hae II.
Figure 6:
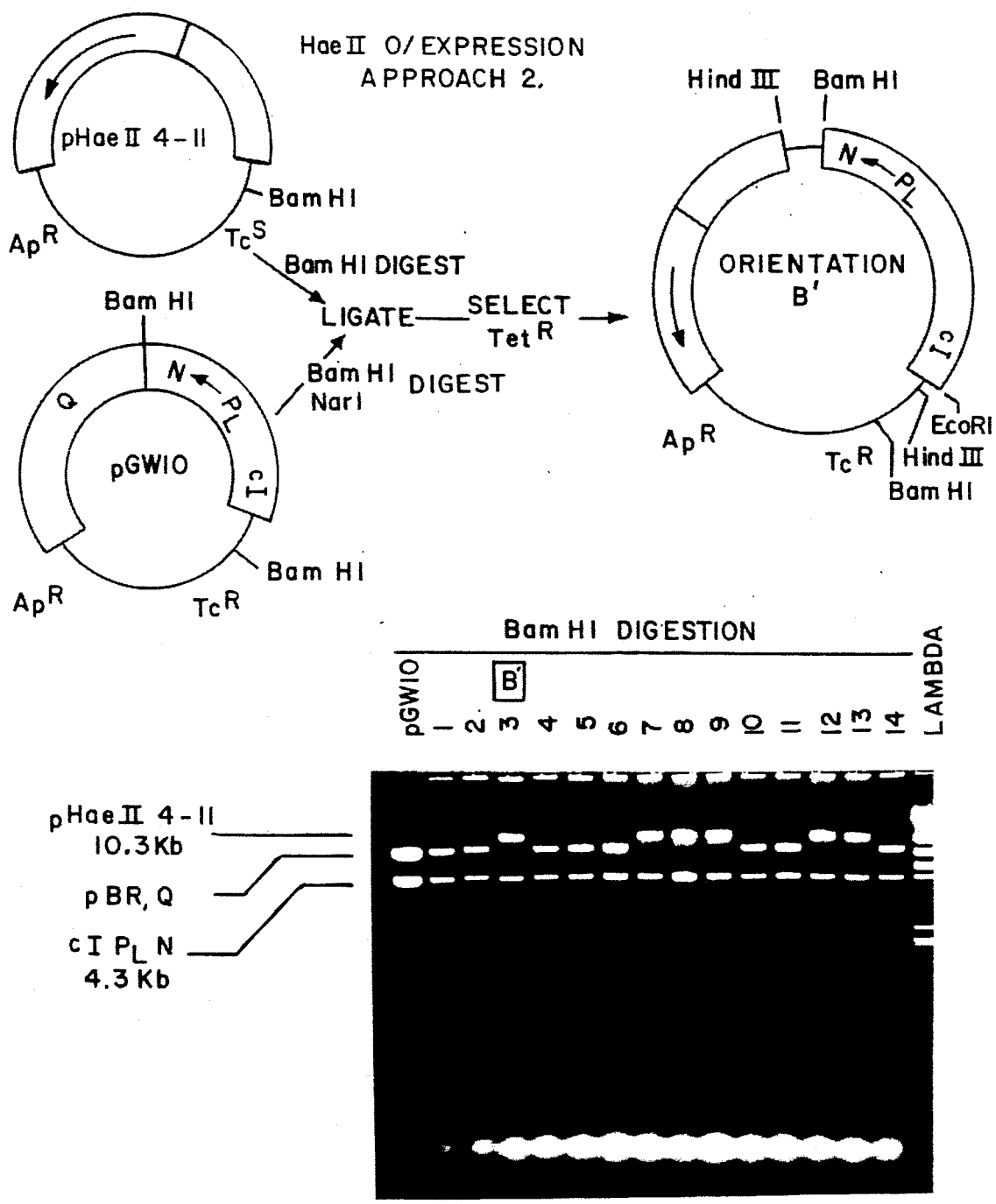
FIG. 6 illustrates a second approach to the overexpression of Hae II.

2. Two different procedures were devised to achieve overproduction (FIGS. 5 and 6). Both procedures involved joining the Hind III fragments to a regulatory element that included a powerful promoter such that when the promoter was derepressed, transcription of the restriction and modification genes would take place at an exceptionally high rate. Such overexpression systems have been previously described.

3. In the first procedure, the 4-11 plasmid was cleaved with Hae III to excise the Hind III fragments together with a little terminal pBR322 DNA, in one segment. The vector pGW7 (ATCC 40166, also available from New England Biolabs) was digested with BamH I and the cohesive BamH I termini filled in with DNA polymerase. For the Hae II plasmid, 12.5 ug of plasmid DNA was mixed with 80 units of Hae III restriction endonuclease in 10 mM Tris, pH 7.5, 10 mM $MgCl_2$, 10 mM mercaptoethanol, 50 mM NaCl, to a final volume of 500 ul. For the pGW7 plasmid, 12.5 ug of plasmid DNA was mixed with 80 units of BamH I restriction endonuclease in the same buffer, but to a volume of 250 ul. The two digestions were incubated at 37° C. for one hour then terminated by heating at 72° C. for 10 minutes. The BamH I digestion was subsequently filled in as follows: To 100 ul of the digestion was added 30 ul of 5X dNTP stock solution (25 mM dCTP, 25 mM dGTP, 25 mM dTTP), 5 ul of 10X Polymerase buffer (100 mM Tris, pH 7.5, 100 mM MgCl$_2$, 10 mMDTT, 500 mM NaCl), 7.5 ul of distilled water, and 7.5 ul of DNA Polymerase Klenow fragment. The reaction was incubated at 20° C. for 15 minutes. 45 ul were then withdrawn and mixed with 45 ul of the 4–11 plasmid digestion, 10 ul of 10X ligation mix (described in Section 3 of Example I) and 5 ul of T4 DNA ligase. The ligation reaction was incubated for 3 hours at 20° C. 10 ul quantities of the ligation were then transformed into E. coli RR1 and plated onto L-agar plates containing ampicillin.

The plates were incubated overnight at 30° C.: The whole ligation yielded 8 plates with approximately 250 colonies/plate, i.e., about 2000 recombinants in all. The plates were scraped and a library of plasmids prepared in the manner described for the preparation of primary plasmid libraries (sections 4 and 5 of Example *). The library was digested with Hae II restriction endonuclease to selectively destroy recombinant plasmids that did not carry the Hae II modification gene. (2.5 units of Exonuclease III was added to each of the digestions to reduce the background of spurious survivors). Following transformation into E. coli RR1, plating of L-agar plates containing ampicillin and incubation at 30° C., surviving colonies were picked and the plasmids that they carried were purified by the miniprep procedure (section 10 of Example I) and then analyzed by digestion and gel electrophoresis. FIG. 5 depicts the entire experimental scheme and also shows a gel of digestions of some of the survivors.

One of the clones isolated by this procedure, designated pHaeII 7–11 was found to carry the Hae II genes in one orientation, B, with respect to the P$_L$ promoter. Several other clones, typical of which is pHaeII 7–6X carried the genes in the other, A, orientation. The clones 7–11 and 7–6X were assayed to determine which, if either, overproduced the endonuclease and the methylase when the external, P$_L$, promoter was depressed by temperature induction. The induction experiments were performed in the following way:

10 ml cultures of the clones were grown overnight at 30° C. in L-broth containing 100 ug/ml ampicillin. The following morning each culture was diluted 50-fold into 500 ml of fresh L-broth and grown in a shaking incubator at 30° C. After approximately 6 hours of incubation, 200 ml of each culture was withdrawn, and its optical density at 590 nm (OD$_{590}$) was measured. The withdrawn cells were collected by centrifugation for 15 minutes at 10K rpm. The rest of each culture was then shifted to a temperature of 43° C. to derepress the P$_L$ promoter. After 3 hours of vigorous shaking at this temperature, the OD$_{590}$ of each culture was again measured and 200 ml of each culture was again collected by centrifugation. The cell pellets were stored at −20° C. until it was convenient to assay them.

To assay for methylase and endonuclease activities, the pellets were thawed and resuspended in sufficient sonication buffer containing 1 mg/ml lysozyme to reach an estimated OD$_{590}$ of 50. The cell suspensions were left on ice for 1 hour then sonicated and assayed as described above (sections 11 and 12 of Example 1).

Clone pHaeII 7–11 was found to overproduce both the Hae II restriction endonclease and the Hae II modification methylase when the culture was shifted to high temperature. Up to $10^6$ units of endonuclease, and $3 \times 10^4$ units of methylase, per gram of wet cell paste, was produced by the 7–11 clone. Conversely, pHaeII 7–6X was found to underproduce both enzymes when the P$_L$ promotor was derepressed. The underproduction is consistent with the reversed orientation that the two genes bear to P$_L$ in this plasmid.

pHae II 7–11 is a new and useful clone from which the Hae II restriciton endonuclease and modification methylase enzymes can be purified in quantity.

4. A second experimental procedure to join the Hae II genes to the overexpression promoter, P$_L$ was devised and carried out. The procedure is simpler and more reliable than the procedure described in the last section, but it yields clones in only one orientation. As it turned out, the orientation it yielded, B, was the one desired. The procedure is outlined in FIG. 6. It used the pGW10 expression vector (ATCC 40167, also available from New England Biolabs), and the desired clones were isolated by direct selection on L-agar plates containing tetracycline. The procedure generated several overproducing plasmids, one of which is pHae II 10-3. After temperature induction, clone 10-3 behaves like 7–11 and overproduces both the methylase and the endonuclease to similar levels as clone 7–11.

Figure 7:
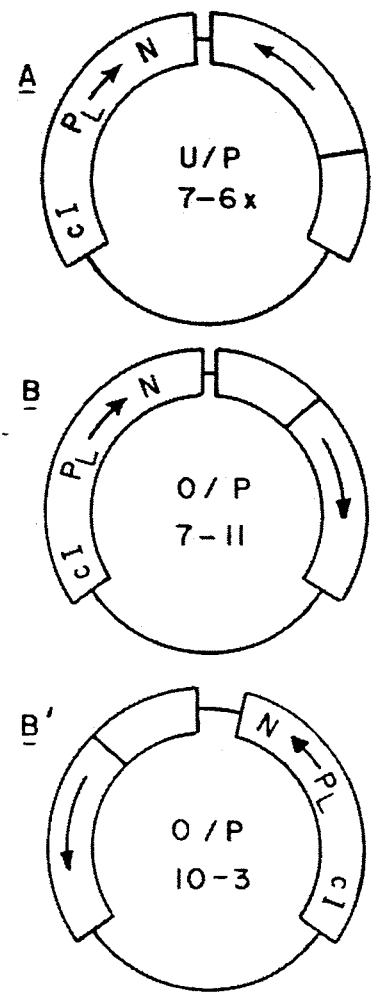
FIG. 7 illustrates under- and over-producing plasmids for Hae II restriction and modification genes and the tabulation of the enzyme yields.
Figure 7:
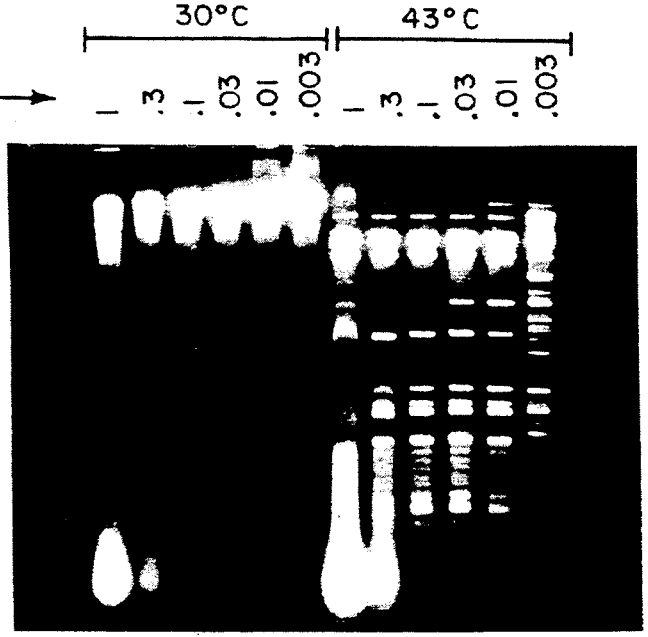

FIG. 7 summarizes the structures of the under- and overproducing plasmids described above and tabulates the enzyme yields.

EXAMPLE III

Cloning of the Tag I Restriction-Modification Genes

1. DNA purification: To prepare the DNA of *Thermus Aquaticus YT*1 (ATCC 25104), 5 gm of freshly-grown cell paste was resuspended in 20 ml of 25% sucrose, 50 mM Tris, pH 8.0. 10 ml of 0.25M EDTA, pH 8.0, plus 6 ml of 10 mg/ml lysozyme in 0.25M Tris, pH 8.0, was added. The suspension was left on ice for two hours, then 24 ml of lysis mix (1% Triton X-100, 50 mM Tris, pH 8.0, 67 mM EDTA) plus 5 ml of 10% SDS was added and mixed to induce cell lysis. 70 ml of freshly-equilibrated phenol was then added and the solution was emulsified by shaking. 70 ml of chloroform was added and the solution was again emulsified by shaking. The mixture was then centrifuged at 10K rpm for 30 minutes and the viscous upper layer, containing DNA, was transferred to a fresh bottle and re-extracted with phenol/chloroform twice more. The upper DNA layer was transferred to dialysis tubing and dialyzed against four changes of 1X DNA buffer (10 mM Tris, 1 mM EDTA, pH 8.0) over 24 hours.

The dialyzed DNA solution was transferred to a beaker and 1/100th volume of 10 mg/ml RNase was added to achieve a final concentration of 100 µg/ml. The solution was incubated at 37° C. for 1 hour to digest the RNA. 5M NaCl was then added to achieve 0.4M final concentration and 0.55 volumes of isopropanol was then layered on top of the solution. The DNA was spooled out of this mixture with a glass rod, then dissolved in 15 ml of 1X DNA buffer and stored at 4° C.

2. Partial digestion: The purified DNA was titrated with BamH I to achieve partial digestion as follows: 2.0 ml of DNA at 100 µg/ml in 10mM Tris pH 7.5, 10mM MgCl$_2$, 10 mM mercaptoethanol, 50mM NaCl buffer was dispensed into ten, 200 µl aliquots. To the first tube was added 200 units of BamH I to achieve 10 units/µg of DNA. To the second tube was added 100 units of BamH I (5 units/µg), and so on, each succeeding tube receiving one half of the previous amount of BamH I.

The tubes were incubated at 37° C. for one hour, then heated to 75° C. for 15 minutes to terminate the reactions. 10 μl from each tube was then analyzed by agarose gel electrophoresis. Tubes exhibiting moderate, but incomplete, digestion were chosen as the source of partially-digested fragments for cloning. (These were the 1.25, 0.63, 0.3 and 0.15 unit/μg tubes. The four solutions were mixed together and used as described below).

3. Ligation: The fragmented DNA was ligated to pBR322 as follows: 6.7 μg of BamH I partially-digested *T. aquaticus* DNA (67 μl) was mixed with 2.5 μg of BamH I-cleaved and dephosphorylated pBR322 (25 μl). 25 μl of 10X ligation mix (500 mM Tris, pH 7.5, 100mM MgCl$_2$, 100 mM DTT, 5mM ATP) was added plus 133 μl of sterile distilled water to bring the final volume to 250 μl. 5 μl of T4 DNA ligase at $4 \times 10^5$ units per ml was added then the mixture was incubated at 17° C. for 4 hours. 20 μl of chloroform was then added and the solution was briefly shaken and centrifuged to terminate the reaction and to sterilize the solution. 100 μl of the solution was mixed with 1.0 ml of SSC/CaCl$_2$ (50mM NaCl, 5mM Na$_3$Citrate, 67 mM CaCl$_2$) on ice and 2.0 ml of ice-cold competent *E.coli* RR1 cells were added. The mixture was heated to 43° C. for 5 minutes then diluted by the addition of 10 ml of Luria-broth (L-broth) and incubated at 37° C. for 4 hours.

4. Primary Cell Library: The transformed culture was centrifuged briefly and the supernatant was discarded. The cell pellet was then resuspended in 2.0 ml of L-broth and 200 μl quantities were plated onto each of 10 Luria-agar (L-agar) plates containing 100 μ/ml ampicillin. After overnight incubation at 37° C., the plates were each flooded with 2.5 ml of 10mM Tris, pH 7.5, 10mM MgCl$_2$ and the transformant colonies were scraped together and pooled to form the primary cell library.

5. Primary Plasmid Library: The primary cell library was prepared as follows: 2.5 ml of the primary cell library was inocculated into 500 ml of L-broth containing 100 μg/ml ampicillin. The culture was shaken overnight at 37° C. then centrifuged at 4K rpm for 5 minutes. The supernatant was discarded and the cell pellet was resuspended in 10 ml of 25% sucrose, 50mM Tris, pH 8.0, at room temperature. 5 ml of 0.25M EDTA, pH 8.0, was added, followed by 3 ml of 10 mg/ml lysozyme in 0.25M Tris, pH 8.0. The solution was left on ice for 1 hour then 12 ml of lytic mix (1% Triton X-100, 50mM Tris, pH 8.0, 67 mM EDTA) was forcefully pipetted in and the cell suspension was gently swirled to achieve lysis. The lysed mixture was transferred to a 50 ml plastic centrifuge tube and spun at 17K rpm, 4° C. for 45 minutes. 22.0 gm of the supernatant was removed by pipet and transferred to a 50 ml plastic screw-cap tube. 20.0 gm of solid CsCl, and 1.0 ml of 5 mg/ml ethidium bromide in 10mM Tris, pH 8.0, 1mM EDTA, 100mM NaCl were added. The tube was gently shaken until all the CsCl had dissolved, then the solution was transferred to two ⅝ in. ×3 in. polyallomer ultracentrifuge tubes. The tubes were sealed then spun in the Ti70 rotor for 42 hours at 50K rpm and 17° C. To collect the plasmids, the tops of the tubes were pierced with a scalpel and the lower of the two fluorescent DNA bands collected by syringe under ultraviolet light. The lower band from both tubes was combined and the ethidium bromide was removed by extracting four times with an equal volume of ice-cold N-Butanol.

The extracted solution was transferred to dialysis tubing and dialyzed for 24 hours against 4 changes of 1X DNA buffer (section 1). The dialyzed DNA solution was then transferred to a pre-weighed 50 ml centrifuge tube and its volume measured. 5M NaCl was added to a final concentration of 0.4M, then 2 volumes of isopropanol was added and mixed. The solution was stored overnight at −20° C. to precipitate the DNA. After precipitation, the solution was spun at 15K rpm, 0° C. for 15 minutes and the supernatant was discarded. The tube was left to air-dry for 15 minutes then 750 μl of sterile distilled water was added. After the pellet had dissolved, 8 μl of 100X DNA buffer was added and the solution was transferred to an Eppendorf tube and stored at −20° C. The plasmid DNA concentration was found to be 150 μg/ml.

6. Digestion of Plasmid Pool: The primary plasmid pool was digested to destroy non-Taq I methylase clones as follows: 150 μl of the plasmid DNA solution was diluted to a volume of 450 μl by the addition of 45 μl of 10X Taq I buffer (100mM Tris, pH 8.4, 60 mM MgCl$_2$, 60 mM Mercaptoethanol, 1M NaCl) and 255 μl of distilled water. The solution was then dispensed into 5 tubes: the first four tubes received 100 μl each and the final tube received 50 μl. 40 units of Taq I was added to the first tube to achieve 8 units of enzyme per μg of DNA. 20 units of Taq I were added to the second tube (4 units/μg) and so on, each tube receiving half of the previous amount. The final tube served as an experimental control and received no Taq I enzyme. The solutions were overlaid with 50 μl of paraffin oil to inhibit evaporation then the tubes were incubated at 65° C. for 1 hour.

7. Transformation: A 10 μl sample from each tube was used to transform *E. coli* RR1 in a manner similar to that described previously: each 10 μl solution was mixed with 100 μl of SSC/CaCl$_2$ (50mM NaCl, 5mM Na$_3$Citrate, 67 mM CaCl$_2$) on ice and 200 μl of ice-cold competent *E. coli* RR1 cells were added. After a 3-minute heat shock at 43° C., the cell/DNA mixtures were immediately plated onto L-agar plates containing 100 μg/ml ampicillin. The plates were incubated overnight at 37° C. then they were examined. Digestion of the plasmid library with Taq I was found to have reduced the number of transformants (i.e. the number of intact plasmids) by a factor of between about $10^3$ and $10^4$. 28 individual colonies from among the survivors on the plates were picked and each was inoculated into 10 ml of L-broth containing ampicillin and streaked onto L-agar plates containing ampicillin.

8. Secondary Population: The remaining colonies were scraped together to form a secondary cell library which was used to prepare a secondary plasmid library in the manner described for the preparation of the primary plasmid library.

9. Analysis of Secondary Plasmid Library: The secondary plasmid library was digested with BamH I and analyzed by gel electrophoresis. A single, prominent 5.5 Kilobase-pair fragment was found to be present within the population.

10. Analysis of secondary individuals: 28 of the surviving colonies among the secondary cell individuals were grown up into 10 ml cultures (section 7) and the plasmids that they carried were prepared by the miniprep purification procedure described in Example I, section 10, above. The plasmid minipreps were analyzed by digestion with Taq I and BamH I.

11. Methylase Gene Clones: Some of the plasmids that were analyzed were found to carry random, BamH I fragments of *T.aquaticus* DNA and to be sensitive to digestion by Taq I. These plasmids were spurious survivors and were of no further interest. The remaining plasmids, however, were found to be resistant to digestion by Taq I and to carry at least one common BamH I fragment of approximately 5.5 Kb in length. All of these plasmids were subsequently shown to carry both the Taq I modification methylase and restriction endonuclease genes. One of these plasmids designated pTaq I 18, is an example of the simplest type of clone: it was found to carry only the one, 5.5 Kb, BamH I fragment. Cells harboring pTaq I 18 were found to synthesize both the Taq I restriction endonuclease and modification methylase in abundance.

The assays to detect Taq I modification methylase activity in vitro were performed as follows:

Methylase Assays: To assay for methylation, three solutions were prepared:

10X Methylation buffer: 0.5M Tris, pH 8.0, 100mM EDTA, 50mM Mercaptoethanol.

Methylation reaction mix: 100 μl lambda DNA at 500 μg/ml, 100 μl 10X methylation buffer, 1 μl 100 mM S-Adenosyl Methionine, 800 μl distilled water.

10X Conversion buffer: 0.5M NaCl, 0.3M $MgCl_2$, 50mM Mercaptoethanol.

Cell extracts: A 100 ml culture was grown overnight at 37° C. in L-broth plus 100 μg/ml ampicillin. The cells were harvested the following morning by centrifugation at 4K rpm for 5 minutes. The supernatant was discarded and the pellet was resuspended in 3.6 ml of sonication buffer (10mM Tris, pH 7.5, 10mM Mercaptoethanol, 1mM EDTA). 0.4 ml of sonication buffer containing 10 mg/ml lysozyme was added and the suspension was swirled and left on ice for 1 hour. A 1 ml sample was then transferred to an Eppendorf tube and sonicated gently for two, 10 second bursts to disrupt the cells. The tube was spun for 30 seconds in a microfuge to pellet the cell debris. The supernatant was transferred to a fresh Eppendorf tube and heated to 65° C. for 20 minutes and the precipitate removed by micro-centrifugation for 30 seconds. The supernatant that remained was used as the cell extract.

Assays: To assay the extract, the methylation reaction mix was prepared fresh and dispensed into 5 tubes, 150 μl into the first tube, and 102.5 μl into each of the remaining 4 tubes. 7.5 μof the cell extract was added to the first tube, mixed and 47.5 μl was removed and added to the next tube, mixed and so on. The first tube thus received 1 μl of extract per μg of DNA, the second tube, 0.3 μl/μg, third tube, 0.1 μl/μg and so on, and each tube finally contained about 100 μl of solution. 50 μl of paraffin oil was layered on top of each solution to inhibit evaporation and the tubes were incubated at 65° C. for one hour. 11 μl of 10X Conversion buffer, and 25 units of Taq I restriction enzyme, were then added to each tube. The solutions were again incubated at 65° C. for one hour then a 20 μl sample of each was analyzed by gel electrophoresis. The clones were found to synthesize about $1 \times 10^5$ units of Taq I methylase per gram of wet cell paste.

12. Restriction Gene Clones: The clones that carried the 5.5 Kb BamH I fragment were found to synthesize the Taq I restriction endonuclease as well as the modification methylase.

The assays to detect Taq I restriction endonuclease activity in vitro were performed as follows:

Endonuclease Assays: To assay for endonuclease activity, two solutions were prepared:

10X Taq I endonuclease buffer: 100mM Tris, pH 8.4, 60 mM $MgCl_2$, 60 mM Mercaptoethanol, 1.0M NaCl.

Endonuclease reaction mix: 100 μl lambda DNA at 500μg/ml, 100 μl 10X Taq I endonuclease buffer, 800 μl distilled water.

Cell extracts: Extracts were prepared in the manner described above for the methylase assays (section 11).

Assays: To assay the extract, the endonuclease reaction mix was prepared fresh and dispensed into 5 tubes, 150 μl into the first tube, and 102.5 μl into each of the remaining 4 tubes. 7.5 μl of the cell extract was added to the first tube, mixed, and 47.5 μl was removed and added to the next tube, mixed and so on. The first tube thus received 1 μl of extract per μg of DNA, the second tube, 0.3 μl/μg, the third tube, 0.1 μl/μg and so on, and each tube finally contained about 100 μl of solution. 50 μl of paraffin oil was layered on top of each solution to inhibit evaporation and the tubes were incubated at 65° C. for one hour. A 20 μl sample of each was analyzed by gel electrophoresis. The clones were found to synthesize about $2 \times 10^5$ units of Taq I restriction endonuclease per gram of wet cell paste. In tests with phages, the clones were not found to resist phage infection to any measurable degree: The efficiency of plating of phage lambda was found to be between 0.5 and 1.

What is claimed is:

1. Isolated DNA coding for the BanI restriction endonuclease, wherein the isolated DNA is obtainable from ATCC Accession No. 75276.

2. A recombinant DNA vector comprising a vector into which a DNA segment coding for the BanI endonuclease produced by *Bacillus aneurinolyticus* has been inserted.

3. Isolated DNA coding for the BanI restriction endonuclease and methylase, wherein the isolated DNA is obtainable from ATCC Accession No. 75276.

4. A cloning vector which comprises the isolated DNA of claim 1.

5. A cloning vector which comprises the isolated DNA of claim 3.

6. The cloning vector of claim 5, wherein the cloning vector comprises ATCC Accession No. 75276.

7. A host cell transformed by the vector of claim 4, 5 and 6.

8. A method of producing BanI restriction endonuclease comprising culturing host cells transformed with the vector of claim 4, 5 or 6 under conditions suitable for the expression of said endonuclease.

* * * * *